United States Patent [19]

Kessel

[11] Patent Number: 5,518,602
[45] Date of Patent: May 21, 1996

[54] AMPEROMETRIC SENSOR

[75] Inventor: Robert Kessel, Bad Oldesloe, Germany

[73] Assignee: Dragerwerk Aktiengesellschaft, Lubeck, Germany

[21] Appl. No.: 502,171

[22] Filed: Jul. 13, 1995

[30] Foreign Application Priority Data

Jul. 15, 1994 [DE] Germany ............ 44 25 135.1

[51] Int. Cl.⁶ .................................................. G01N 27/26
[52] U.S. Cl. ...................... 204/415; 204/412; 204/431; 204/432
[58] Field of Search ............................ 204/412, 415, 204/431, 432

[56] References Cited

U.S. PATENT DOCUMENTS 4,552,624  11/1985  Clarkson ..................... 204/431

OTHER PUBLICATIONS

"Amperometric acidic gas sensors using platinum oxide reduction and iodine reduction" by T. Ishiji, Sensors and Actuators B, vol. 13–14, (1993) pp. 583 and 584.

*Primary Examiner*—Bruce F. Bell
*Attorney, Agent, or Firm*—Walter Ottesen

[57] ABSTRACT

An amperometric sensor detects acidic and alkaline gases utilizing a first pH-dependent reversible redox system on a measuring electrode 4. A reduction current occurs between the measuring electrode 4 and a counter electrode 6 for a constant potential and is used as a measurement variable of the concentration of the gas to be detected. In addition, a reference electrode 5 is disposed in an electrolyte 7 together with the measuring electrode 4 and the counter electrode 6. The gas to be detected penetrates through the permeable membrane 2 and is dissolved while being dissociated. The amperometric sensor is improved with respect to its permanent stability. This is provided in that the first pH-dependent redox system is coupled to a second redox system and the redox potential of the second redox system is so selected that the reaction product is chemically regenerated again to the educt via the second redox system. The reaction product is electrochemically formed at constant potential by the first redox system.

17 Claims, 2 Drawing Sheets

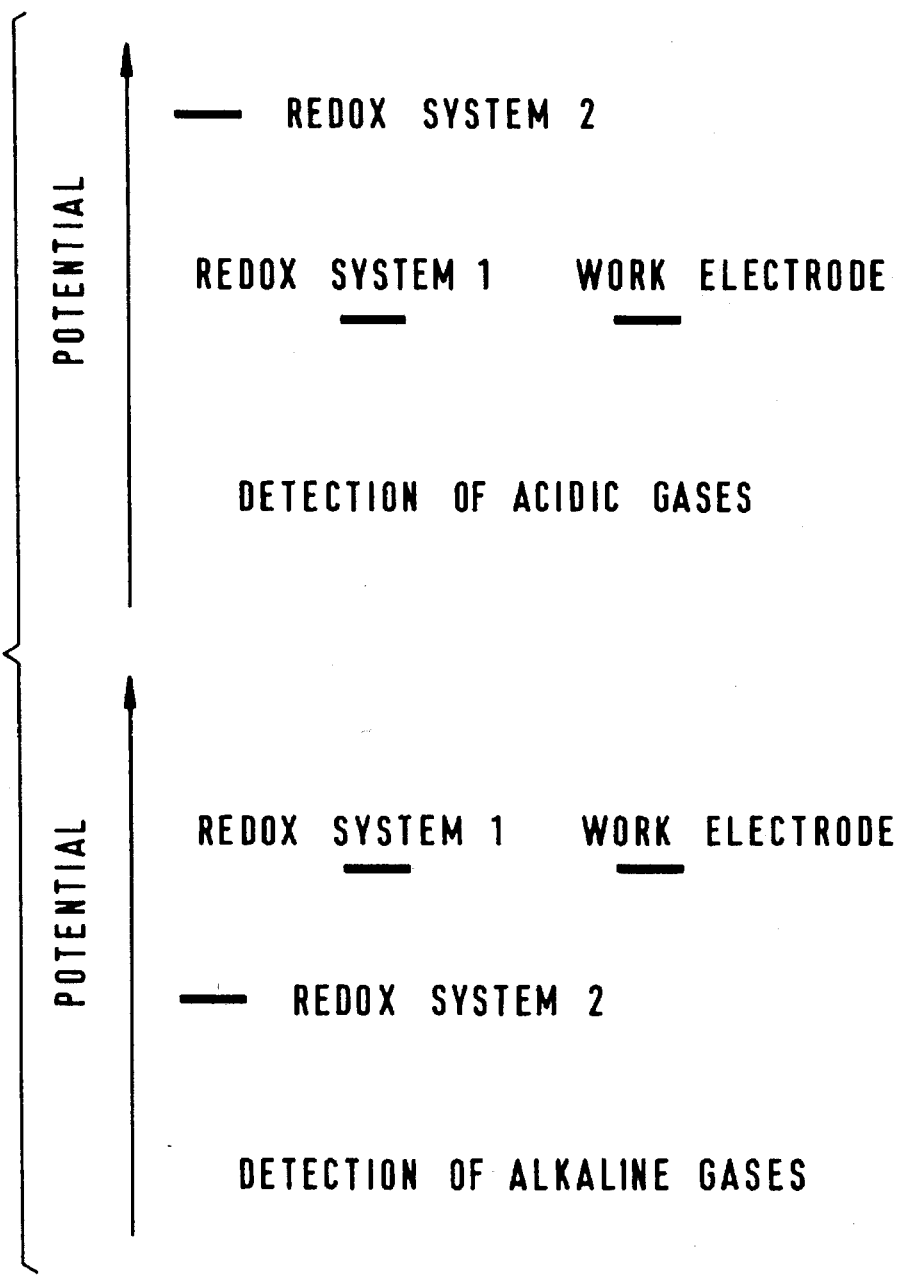

AMPEROMETRIC SENSOR

FIELD OF THE INVENTION

The invention relates to an amperometric sensor for detecting acidic and alkaline gases while utilizing a pH-dependent reversible redox system on a measuring electrode. The reduction current occurring between the measuring electrode and a counter electrode at constant temperature is used as a measurement variable of the concentration of the gas to be detected. The sensor further includes a reference electrode which, together with the measuring electrode and the counter electrode, is present in an electrolyte wherein the gas to be detected is dissolved by dissociation. The gas to be detected penetrates through a permeable membrane.

BACKGROUND OF THE INVENTION

A sensor of the kind referred to above is described by T. Ishiji et al in an article entitled "Amperometric Acidic Gas Sensors using Platinum Oxide Reduction and Iodine Reduction", published in the journal "Sensors and Actuators B", 13–14 (1993), pages 583 and 584. The measuring or work electrode is defined by a sputter coating on a gas-permeable membrane made of polytetrafluorethylene (PTFE). The sputter coating is formed by vapor depositing a thin coating of platinum oxide. The counter electrode and the reference electrode are silver wires. A 0.1 M aqueous KCl solution is used as an electrolyte. Such a platinum sensor is used, inter alia, to detect carbon dioxide ($CO_2$). However, it has been shown that the precious metal oxide, which is available only in limited quantities, is rapidly consumed during operation of the sensor. Thereafter, the measurement signal collapses.

A known method for detecting acidic and alkaline gases is based upon the potentiometric measurement with ion-specific electrodes. Here, it appears to be disadvantageous that the potentials of the measurement electrode and the reference electrode must be held very stable. Even slight deviations significantly affect the precision of the measurement. The gas to be detected accumulates in the electrolyte during long time spans of operation and continuous exposure to the gas. If the gas concentration is then subsequently reduced, an adjustment of the new equilibrium value takes place extremely slowly.

A further known method for detecting acidic gases comprises shifting a redox equilibrium by means of a pH change. Here, the position of a redox equilibrium is changed by the entry of the acidic gas into the electrolyte. In this way, a current is generated for a potentiostatic circuit of the measuring electrode and this current is proportional to the concentration of the gas to be detected. In this method, the equilibrium shift of the redox reaction is utilized for detection and does not only occur because of the change of the pH value, but also because of temperature jumps. Furthermore, the detection sensitivity appears to be satisfactory only for intensely acidic gases.

A sensor disclosed in U.S. Pat. No. 4,552,624 also belongs to the known state of the art. The electrolyte comprises a mixture of bromide and bromate. The dissociated gas dissolved in the electrolyte reacts directly with the electrolyte and free bromine occurs from the comproportionation of the educts. The bromine is then electrochemically detected on a metallic measuring electrode. It is disadvantageous in this method that an adequate sensitivity is obtained only with intensely acidic gases.

SUMMARY OF THE INVENTION

It is an object of the invention to provide an amperometric sensor of the kind described above which is so configured that the sensor makes longer operating times possible and also reacts with adequate rapidity to concentration changes of the gases to be detected.

The amperometric sensor of the invention is for detecting acidic and alkaline gases. The amperometric sensor includes: a housing having an opening directed toward the gas to be detected and defining an electrolyte chamber; a permeable membrane covering the opening and through which the gas penetrates to enter the chamber; an electrolyte contained in the chamber in which the gas is dissolved while dissociating; a measuring electrode, a counter electrode and a reference electrode disposed in the electrolyte in spaced relationship to each other; circuit means for maintaining a constant potential across the measuring electrode and the reference electrode; a first redox system on the measuring electrode for electrochemically forming a reaction product while the potential is maintained constant; the first redox system being a pH-dependent reversible redox system; a second redox system coupled to the first redox system and having a redox potential selected so as to cause the second redox system to again chemically regenerate the reaction product to the educt; and, means for detecting a reduction current occurring between the measuring electrode and the counter electrode at the constant potential with the reduction current being used as a measurement variable indicative of the concentration of the gas.

The potential of the second redox system can advantageously be so adjusted with respect to the potential of the measuring electrode that the second redox system is not converted on the measuring electrode. As a pH-dependent redox system, a metal oxide can advantageously be used which reacts reversibly with protons from the dissolved and dissociated gas. In this configuration, the oxide, which is consumed by the electrochemical conversion, is recovered on the measuring electrode by chemical conversion so that, for precious metal oxides, no loss of the relatively valuable precious metal oxide occurs.

The second redox system can be configured so as to be pH-dependent as well as pH-independent. It furthermore appears advantageous to add the second redox system in excess compared to the stoichiometric determination because this second redox system is consumed during operation of the sensor and could otherwise produce a drop of the oxidation potential.

In a further embodiment of the invention, the measuring electrode potential is so selected that it is below the redox potential of the second redox system for acidic gases and is above the redox potential of the second redox system for alkaline gases. In this way, an excellent regeneration effect is obtained.

The first redox system is advantageously a metal oxide, preferably of the platinum group, which is generated directly on the surface of the measuring electrode and is thereby spatially fixed with respect to the electrolyte.

In an advantageous embodiment, the first redox system can be an iridium oxide coating ($IrO_2$) on an iridium substrate.

The electrolyte can advantageously contain a halogenate salt as a second redox system to detect an acidic gas. This halogenate salt (or, if required, a mixture of various salts) can, as a supporting electrolyte, include an alkali halogenide, an alkali earth halogenide or an ammonium halogenide.

The electrolyte can advantageously contain lithium chloride with an admixture of potassium iodate. In another composition, the electrolyte can contain a bromate.

The reference electrode of the sensor can advantageously comprise silver or precious metal. For the counter electrode, a configuration of silver, precious metal or lead appears to be advantageous.

In a tested embodiment, the electrolyte comprised a 3 to 10 M aqueous solution of lithium chloride with an admixture of potassium iodate from 0.01 M to saturation.

The running reactions can be described as delineated below.

First, the gas, such as $CO_2$, which penetrates through the membrane into the aqueous electrolyte, reacts as follows:

$$CO_2 + H_2O \leftrightarrows H^+ + HCO_3^-$$

The $H^+$ ion reacts then with the first redox system, that is, with the oxide (for example, with iridium oxide $IrO_2$) of the measuring electrode. The reaction in an electrochemical operation runs as follows:

$$IrO_2 + H^+ + e^- \leftrightarrows IrOOH$$

Thereafter, the reduction product IrOOH is again chemically oxidized by the second redox system:

$$6\ IrOOH + IO_3^- \leftrightarrows 6\ IrO_2 + I^- + 3\ H_2O$$

In this operation, the higher quality oxide is always recovered so that even extremely thin oxide coatings of less than a few micrometers (μm) are adequate for the configuration of the sensor because, in the total reaction, only the very inexpensive chemical oxidation agent of the second redox system is consumed.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
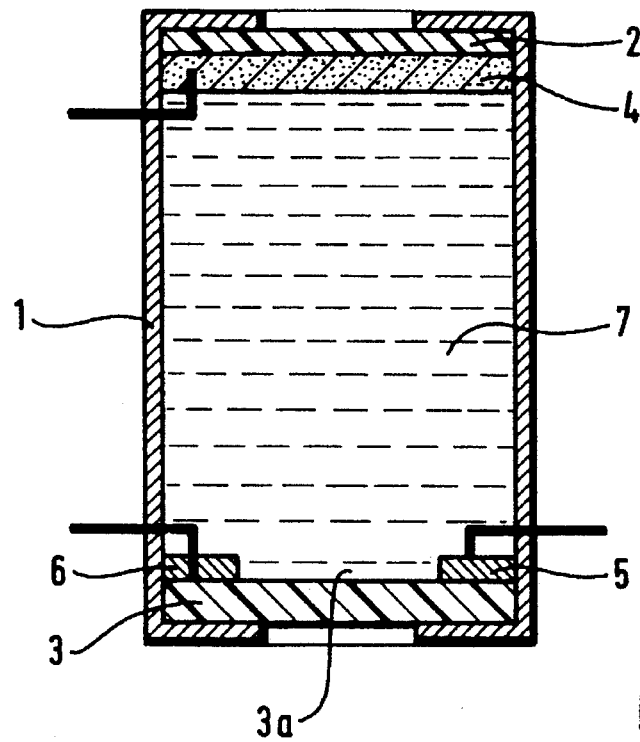
FIG. 1 is a longitudinal section view taken through an amperometric sensor according to the invention.

The amperometric sensor shown in FIG. 1 includes a tube-shaped housing 1 having gas-permeable polytetrafluorethylene membranes (2, 3) at respective ends. The membrane 2 is at the gas inlet end and is provided on its inner side with a porous, gas-permeable iridium coating which is oxidized to $IrO_2$ on its surface. This iridium oxide coating defines the measuring electrode 4. A reference electrode 5 of silver and a counter electrode 6 of metallic iridium are applied to the inner side of the opposite-lying membrane 3. The electrolyte 7 is disposed in the free interior space of the tube-shaped housing between the measuring electrode 4, the reference electrode 5, the counter electrode 6 and the free cutout 3a.

This electrolyte 7 comprises a 3 to 10 M aqueous solution of lithium chloride (LiCl) with an admixture of 0.01 to 0.2 M potassium iodate ($KIO_3$).

Practical experiments with the amperometric sensor described above have shown that a change in current of between 5 and 18 μA occurs for a change of the $CO_2$ concentration between 0.5 and 1.5% by volume. The stability of the amperometric sensor during continuous exposure to a gas is adequate for practical application purposes and a regeneration can, if required, take place with an exchange of electrolyte.

Figure 2:
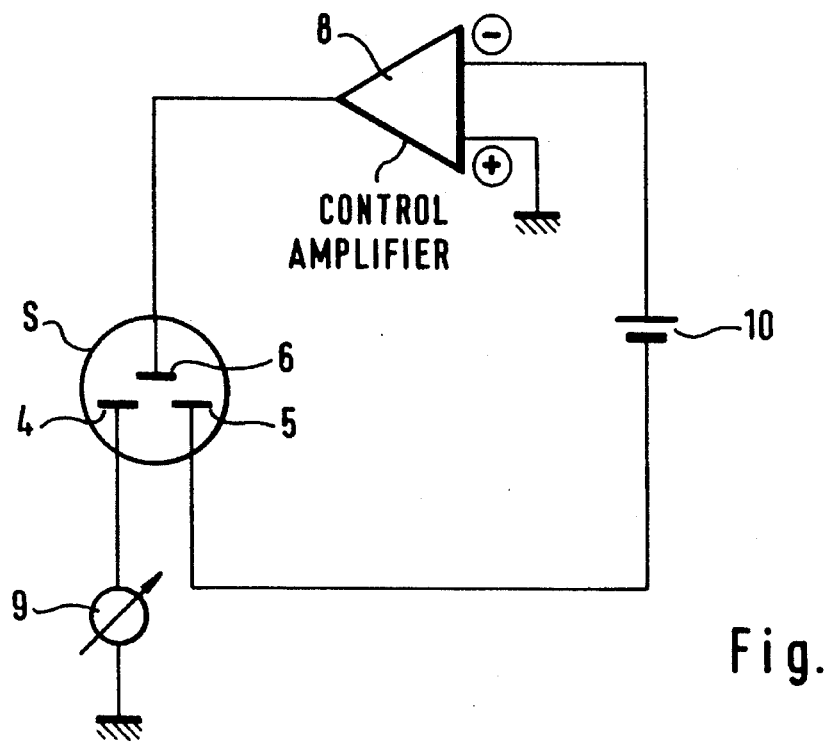
FIG. 2 is a circuit schematic for an amperometric sensor of the kind shown in FIG. 1; and, FIG. 3 is a schematic representation of the potentials of the redox systems.

FIG. 2 is a schematic representation of a switching arrangement for the amperometric sensor S. This circuit is a so-called potentiostat circuit having a control amplifier 8 which operates to maintain the potential constant between the measuring electrode 4 and the reference electrode 5. The current between the measuring electrode 4 and counter electrode 6 required for maintaining the potential constant is detected as a measuring variable with the aid of a μA meter 9. A constant voltage source 10 is provided for supplying the control circuit.

FIG. 3 shows a schematic representation of the potentials of the redox systems.

Before entry of the acidic gas into the electrolyte, the potential of the first redox system is specified by the pre-given potential of the work or measuring electrode. This potential is so selected that it is less than the equilibrium potential of the second redox system but so that no electrochemical reaction of the second redox system with the measuring electrode occurs. The pH value of the solution, and therefore the potential of the first redox system, changes because of the dissociation of the acidic gases in the water. From this, a cathodic current results on the measuring electrode. The suboxide of iridium (IrOOH) is formed as a consequence of this electrochemical reaction and can then subsequently be reoxidized to iridium dioxide ($IrO_2$) by a chemical reaction with the second redox system which functions as oxidation agent for the formed IrOOH.

The potential position of the redox system for the detection of alkaline gases is shown in the lower portion of FIG. 3. Here, the potential of the second redox system is less than the potential of the measuring electrode.

It is understood that the foregoing description is that of the preferred embodiments of the invention and that various changes and modifications may be made thereto without departing from the spirit and scope of the invention as defined in the appended claims.

What is claimed is:

1. An amperometric sensor for detecting acidic and alkaline gases, the amperometric sensor comprising:

a housing having an opening directed toward the gas to be detected and defining an electrolyte chamber;

a permeable membrane covering said opening and through which the gas penetrates to enter said chamber;

an electrolyte contained in said chamber in which said gas is dissolved while dissociating;

a measuring electrode, a counter electrode and a reference electrode disposed in said electrolyte in spaced relationship to each other;

circuit means for maintaining a constant potential across said measuring electrode and said reference electrode;

a first redox system on said measuring electrode for electrochemically forming a reaction product while said potential is maintained constant;

said first redox system being a pH-dependent reversible redox system;

a second redox system coupled to said first redox system and having a redox potential selected to cause said second redox system to again chemically regenerate said reaction product to the educt; and, means for detecting a reduction current occurring between said measuring electrode and said counter electrode at said constant potential with said reduction current being used as a measurement variable indicative of the concentration of said gas.

2. The amperometric sensor of claim 1, wherein the potential of said second redox system relative to said measuring electrode is selected so that said second redox system is not converted at said measuring electrode.

3. The amperometric sensor of claim 1, wherein said second redox system is added in excess, compared to stoichiometric determination, to said electrolyte.

4. The amperometric sensor of claim 1, wherein the potential on said measuring electrode is selected to be less than said redox potential of said second redox system for acidic gases and above said redox potential of said second redox system for alkaline gases.

5. The amperometric sensor of claim 1, wherein said first redox system is a metal oxide of the platinum group.

6. The amperometric sensor of claim 5, wherein said first redox system includes iridium oxide.

7. The amperometric sensor of claim 6, wherein said iridium dioxide is an oxide coating fixed on an iridium substrate and is spatially fixed in said electrolyte.

8. The amperometric sensor of claim 5, wherein, for detecting an acidic gas, said electrolyte includes a halogenate salt as said second redox system.

9. The amperometric sensor of claim 8, said electrolyte containing a supporting salt selected from the group consisting of alkali halogenide, alkali earth halogenide and ammonium halogenide.

10. The amperometric sensor of claim 8, wherein said electrolyte includes lithium bromide.

11. The amperometric sensor of claim 10, wherein said electrolyte includes an admixture of potassium iodate.

12. The amperometric sensor of claim 8, wherein said electrolyte includes lithium chloride.

13. The amperometric sensor of claim 12, wherein said electrolyte includes an admixture of potassium iodate.

14. The amperometric sensor of claim 8, wherein said electrolyte includes a bromate.

15. The amperometric sensor of claim 8, wherein said electrolyte comprises a 3 to 10 M aqueous solution of lithium chloride with an admixture of 0.01 M to saturation of potassium iodate.

16. The amperometric sensor of claim 1, wherein said reference electrode comprises silver or a precious metal.

17. The amperometric sensor of claim 1, wherein said counter electrode comprises a metal selected from the group consisting of silver, precious metal and lead.

* * * * *